United States Patent
Guadagno et al.

(10) Patent No.: US 6,395,727 B1
(45) Date of Patent: May 28, 2002

(54) METHOD OF TREATING BULIMIA NERVOSA AND RELATED EATING DISORDERS BY ADMINISTRATION OF ATYPICAL ANTIPSYCHOTIC MEDICATIONS

(75) Inventors: Gina Guadagno; Jodi M. Star, both of Cincinnati, OH (US)

(73) Assignee: The Cincinnati Children's Hospital Research Foundation, Cincinnati, OH (US)

( * ) Notice: Subject to any disclaimer, the term of this patent is extended or adjusted under 35 U.S.C. 154(b) by 0 days.

(21) Appl. No.: 09/531,129

(22) Filed: Mar. 17, 2000

Related U.S. Application Data

(60) Provisional application No. 60/124,952, filed on Mar. 18, 1999.

(51) Int. Cl.$^7$ .......................... A61K 31/55; A61K 31/505
(52) U.S. Cl. .................. 514/211.06; 514/273; 514/220; 514/258
(58) Field of Search ................................ 514/331, 373, 514/211.06, 220, 258

(56) References Cited

U.S. PATENT DOCUMENTS 6,214,846 B1 * 4/2001 Elliott ........................ 514/331

FOREIGN PATENT DOCUMENTS

| WO | WO9638152 | 12/1996 |
| WO | WO9732037 | 9/1997 |
| WO | WO9804289 | 2/1998 |

OTHER PUBLICATIONS

Agras WS. Pharmacotherapy of bulimia nervosa and binge eating disorder: longer term outcomes. Psychopharmacology Bulletin. 1997;33:433–436.
*American Psychiatric Association. Diagnostic and Statistical Manual of Mental Disorders, 4th ed. Washington, DC: American Psychiatric Association; 1994; 539–550.
Barry VC, Klawans HL. On the role of dopamine in the pathophysiology of anorexia nervosa. J Neural Transm. 1976;38:107–122.
* Bebee DW, Homebeck GN, Grzeskiewicz B. Non–native and psychometic data in body image assessment revised. 1999 Pending publication.
Blouin JH, Carter J, Blouin AG, Tener L., Prognostic indicators in bulimia nervosa treated with cognitive behavioral therapy. Int'l J of Eating Disorders. 1994; 15(2):113–123.
Bruch H. Perceptual and conceptual disturbances in anorexia nervosa. Psychosom Med. 1962;24:187–194.
Carney CP, Andersen AE. Eating disorders: guide to medical evaluation and complications. The Psychiatric Clinics of North America. 1996;19(4):657–679.
Crockford, David N., Risperidone, Weight Gain, and Bulimia Nervosa, The Canadian Journal of Psychiatry, 42:3, Apr. 1997; pp. 326–327.

DuBois FS. Compulsion neurosis with cachexia. Am J of Psychiatry. 1949;106:107–115.
Eisen JL, Phillips KA, Baer L, Beer DA, Atala KD, Rasmussen SA. The brown assessment of beliefs scale: reliability and validty. Am J of Psychiatry. 1998; 1 5 5(l); 1 02108.
Faltus F. Pimozide in the treatment of psychogenic disorders. Ceskoslovenska Psychiatrie. 1993; 24–26.
Fisman, Sandra, et al., Case Study: Anorexie Nervos and Autistic Disorder in an Adolescent Girl, J. Am. Acad. Child Adolesc. Psychiatry, 35:7, Jul. 1996; pp. 937–940.
Freeman CP, Munro JK. Drug and group treatment for bulimia nervosa. J of Psychosomatic Research. 1998;36:647–660.
Gillberg C. Low dopamine and serotonin levels in anorexia nervosa. Am J Psychiatry. 1982; 140:948–949.
Goldstein DJ, Wilson MG, Ascroft RC, Al–Banna M. Effectiveness of fluoxetine therapy and bulimia nervosa regardless of comorbid depression. Int J of Eating Disorders. 1999; 25 (1): 19–27.
Gutierrez–Esteinou R, Grebb JA. Risperidone:an analysis of the first three years in general use. International Clinical Psychopharmacology. 1997;12:S3–10.
Gwirtsman HE. Overview of the definition, prevalence, and comorbidity of bulimic disorders. Psychopharmacology Bulletin. 1993;29:109–114.
Hall RC, DulapPK, Pacheo CA, Blakey RK, Abraham J. Thyroid disorder and abnon–nal thyroid function test in women with eating disorder and depression. J of the Florida Medical Association. 1995;82(3): 187–92.
Herzog DB, Nussbaum KM, Man–nor AK. Comorbidity and outcome in eating disorders. The Psychiatric Clinics of North America. 1996;19:843–859.
Hillert A, Maier W, Wefzel H, Benkert O. Risperidone in the treatment of disorders with a combined psychotic and depressive syndromes functional approach. Phan–nacopsychiat. 1992;25:213–217.
Jimerson DC, Lesem MD, Kaye WH, Brewerton TD. Low serotonin and dopamine . metabolite concentration in cerebrospinal fluid from bulimic patients with frequent binge episodes. Archives of General Psychiatry. 1992;49:132–138.

(List continued on next page.)

Primary Examiner—Theodore J. Criares
(74) Attorney, Agent, or Firm—Loy M. White; Steven J. Goldstein

(57) ABSTRACT

The invention relates to a method of treating non-psychotic disorders by administration of atypical antipsychotic medications, in particular, risperidone. More specifically, the invention relates to a method of treating the eating disorder Bulimia Nervosa and Bulimia-related eating disorders, by administration of antipsychotic medications from the group of compounds designated as atypical antipsychotic mediations. Typical dosage amounts may range from 0.1 milligrams to 4 milligrams per day and may be administered in any dosage forms known in the art, including, but not limited to oral, intramuscular, rectal, transdermal, sustained release forms, controlled release forms, delayed release forms, and response release forms.

20 Claims, No Drawings

OTHER PUBLICATIONS

Kaplan AS, Garfinkle PE, Darby PC, Garner DM. Carbamazepine in the treatment of bulimia. Am J of Psychiatry. 1983;40(9): 1225–1226.

Keel PK, Mitchell JF. Outcome in bulimianer–vosa. Am J Psychiatry. 1997;154:313–321.

Kleinberg DL, Davis JM, de Coster R, Van Baelen B, Brecher M. Prolactin levels and adverse events in patients treated with risperidone. J Clin Psychopharmacol. 1999; 1 9:576 I.

Kleifield El, Vagners S, Halmi K. Cognitive behavioral treatment of anorexia nervosa. Psychiatric Clinics of North America. 1996–19:715–737.

Kumra S, Herion D, Jacobson L, Briguglia C, Grothe D. Case study; risperidone induced hepatoxicity in pediatric patients. J Am Acad Child Adolesc Psychiatry. 1997–36:701–705.

* Lane HY, Chang WH. J Clin Psychopharmacology. 1998; 59: 11.

Lombroso PJ, Scahill L, King RA, Lynch KA, Chappell PB, Peterson BS, McDougle CJ, Leckman JF. Risperidone treatment of children and adolescents with chronic tic disorders: a preliminary report. J Am Acad Child Adolesc Psychiatry. 1995; 34:11471152.

Marrazzi MA, Bacon JP, Kinzie J, Luby ED. Naltrexone use in the treatment of anorexia nervosa and bulimia nervosa. Int Clinical Psychopharmacology. 1995;10(3):163–72.

McDougle CJ, Holmes JP, Carlson DC, Pelton GH, Cohen DJ, Price LH. A double blind, placebo controlled study of risperidone in adults with autistic disorder and other pervasive developmental disorders. Archives of General Psychiatry. 1998;55:633–641.

Mueller–Slecheneder F, Mueller M, Hillert A, Szegedia A, Wetzel H, Benkert O. Risperidone versus haliperidol and amitriptyline in the treastment of patients with a combined psychotic and depressive syndrome. J of Clin Psychophann. 1998; 1 8(2):1 1 1 . 120.

Nicolson R, Awad G. Sloman L. An open trial of risperidone in young autistic children. J Am Acad Child Adolesc Psychiatry. 1998;37:372–376.

Owens DG. Extrapyramidal side effects and tolerability of risperidone: a review. J of Clin Psychiatry. 1994;55S:29–35.

Phillips KA, Kim JM, Hudson JI. Body Image disturbance in body dysmorphic disorder and eating disorders obsession or delusions. The Psychiatric Clinics of North America. 1995;18:317–334.

Saxena S, Wang D, Bystritsky A, Baxter LR. Risperidone augmentation of SRI treatment for refractory obsessive––compulsive disorder. J Clin Psychiatry. 1996;57(7):303–6.

* Schreier HA. Risperidone for young children with mood disorders and aggressive behavior. J of Child and Adolesc Psychopharmacology. 1998;8:49–59.

Segal J, Berk M, Brook S. Risperidone compared with both lithium and haloperidol in mania: a double–blind randomized controlled trial. Clinical Neuropharmacology. 1 998;21:176–180.

Spatz N, Spatz H, Mesones Arroyo HL, Rosan T, Brengio F. Elimination of n,ndimethyltryptamine by urine. Acta Psiquiatrica y Psicologica de America Latina. 1993;39:212–216.

Stunkard A. Eating disorders: the last twenty–five years. Appetite. 1997;29(2):181–90.

Toren P, Laor N, Welzman A. Use of atypical neuroleptics in child and adolescent psychiatry. J of Clinical Psychiatry. 1998; 59:644–656.

Vandereycken W, Plerloot R. Pimizide combined with behavior therapy in the short–term treatment of anorexia nervosa. A double–blind placebo controlled cross–over study. Acta Psychiatr Scand. 1982;66:445–450.

*VanKammen DP, Marder: Biological therapies. In Kaplan and Sadock's Comprehensive Textbook of Psychiatry, ed 7, Sadock BJ, Sadock V editors. Williams and Wilkins; Philadelphia, p. 2465.

Vieta E, Gasto C, Colom F, Martinez A, Otero A, Vallejo J. J of Clin Psychopharmacology. 1998;18(2):172–173.

Walsh BT, Delvin MJ. Pharmacotherapy of bulimia nervosa and binge eating disorder. Addictive Behaviors. 1995; 20(6):751–764.

Walsh BT, Devlin MJ. The pharmacologic treatment of eating disorders. The Psychiatric Clinics of North America. 1992; 1 5:149–160.

* Wermuth BM, Davis KL, Hollister LE. Phenytoin treatment of binge–eating syndrome. Am J Psychiatry 1997; 134: 1249–1253.

Yates A. Current perspectives on the eating disorders: history, psychological and biological aspects. J Am Acad Child Adolesc Psychiatry. 1989;6:813–828.

Zarate CA, Baldessarini RJ, Siegel AJ, Nakamura A, McDonald J, Muir–Hutchinson LA, Cherkerzian T, Tohen M. Risperidone in the elderly: a pharmacoepidemiologic study. J Clin Psychiatry. 1997; 58:311–317.

* cited by examiner

METHOD OF TREATING BULIMIA NERVOSA AND RELATED EATING DISORDERS BY ADMINISTRATION OF ATYPICAL ANTIPSYCHOTIC MEDICATIONS

This application claims the benefit of Provisional Application No. 60/124,952 filed Mar. 18, 1999.

TECHNICAL FIELD

The present invention relates to a method of treating non-psychotic disorders by administration of antipsychotic medications. More specifically, the present invention relates to a method of treating the eating disorder Bulimia Nervosa, and bulimia-related eating disorders, by administration of antipsychotic medications from the group of compounds designated as "atypical" antipsychotic medications. In particular, this invention contemplates use of the atypical antipsychotic medication risperidone for treatment of Bulimia Nervosa and bulimia-related disorders.

BACKGROUND OF THE INVENTION

I. Bulimia Nervosa and Related Eating Disorders

Bulimia Nervosa ("ox like hunger of nervous origin") was identified as a mental disorder in the early 1970's, but was considered to be an "ominous" variation of the then more recognized eating disorder, anorexia nervosa. Subsequent developments in the study of eating disorders has indicated that, although many anorexia nervosa patients are, or may become bulimic, Bulimia Nervosa is a separate disorder with a distinct set of clinically-defined symptoms and behaviors. The disorder anorexia nervosa can be generally characterized by an individual's refusal to maintain a minimally normal body weight usually effectuated through severe restriction of caloric intake. In contrast, Bulimia Nervosa and bulimia-related eating disorders are generally characterized by repeated episodes of binge eating, followed by inappropriate and unhealthy compensatory behaviors such as self-induced vomiting; misuse of laxatives, diuretics, or other medications; fasting or excessive exercise.

Bulimia Nervosa is of unknown etiology, but it affects a relatively large portion of the population. The Diagnostic and Statistical Manual of Eating Disorders, $4^{th}$ ed., (DSM-IV), reports the prevalence of Bulimia Nervosa to be 1% to 3% within the adolescent and young adult female population, and one-tenth of that in the male population. No reliable statistics are available regarding the prevalence of bulimia-type eating disorders in these populations, but it is believed that the rate is similar, or greater, than that of Bulimia Nervosa. Bulimia Nervosa has been reported to occur with roughly similar frequencies in most industrialized countries, including the United States, Canada, Europe, Australia, Japan, New Zealand and South Africa. Thus, within the female population of industrialized nations, Bulimia Nervosa is at least as common as other major psychiatric disorders such as schizophrenia, which occurs at a rate of 1.5%, and Major Depressive Disorder, which occurs at a rate of 1.3%.

The essential features of Bulimia Nervosa are a disturbance in perception and a high level of preoccupation with body shape and weight, coupled with binge eating and inappropriate compensatory methods to prevent weight gain. Other characteristic behaviors, as well as the physical and psychological symptoms which give rise to a diagnosis of Bulimia Nervosa, are well-known in the art and are detailed in the DSM-IV at pages 545 to 550, the contents of which are incorporated herein by reference.

The diagnostic criteria for Bulimia Nervosa are highly defined; for a diagnosis of Bulimia Nervosa, individuals must exhibit particular behaviors and psychological symptoms with specified frequency. Frequently individuals engaging in disordered eating practices do not meet these DSM-IV criteria, but exhibit behaviors and thought patterns common to individuals diagnosed with Bulimia Nervosa, including binge eating, followed by compensatory behaviors and an undue preoccupations with body shape. These individuals are defined by the DSM-IV as having a Bulimia-Type Eating Disorder Not Otherwise Specified (Eating Disorder N.O.S.). The specific clinical criteria defining Bulimia-Type Eating Disorders N.O.S. are well-known in the art and are detailed in the DSM-IV at page 550, the contents of which are incorporated herein by reference.

The average age for the onset of Bulimia Nervosa or Bulimia-Type Eating Disorder N.O.S. is late adolescence or early childhood. The overwhelming majority of those who are afflicted, approximately 98%, are young women. In a high percentage of cases, the disturbed eating behavior persists for several years. Recovery rates for Bulimia Nervosa have been reported at 38% to 46%. The long-term outcome of Bulimia Nervosa is not known, but anecdotal evidence suggests that relapse is common.

Early epidemiological and family studies of eating disordered individuals demonstrated an apparent linkage between such disorders and mood disturbances. This initial observation has been reinforced further by clinical and physiological data. For example, studies of individuals diagnosed with Bulimia Nervosa have indicated a high frequency of comorbid diagnoses of axis I psychiatric disorders, including Major Depressive Disorder, and Bulimia Nervosa or Bulimia-Type Eating Disorder N.O.S. Further, research into the pathophysiological bases of eating disorders has implicated a disturbance in the serotonigenic system of eating disordered individuals, a neurotransmitter system also believed to play a role in mood disorders. Because of the several associations of Bulimia Nervosa and Bulimia-Type Eating Disorder N.O.S. with mood and anxiety disorders, most of the treatment modalities devised for Bulimia Nervosa and Bulimia-Type Eating Disorder N.O.S. have been developed from, or have been related to, treatment approaches developed for these disorders. In fact, a brief survey of the scientific literature reveals that, although they are not clinically defined as mood or anxiety disorders, Bulimia Nervosa and Bulimia-Type Eating Disorders N.O.S. are frequently treated with antidepressant medications, such as fluoxetine, imipramine and trazodone.

II. Atypical Antipsychotic Medications

Beginning in the early 1950's, a group of neuroleptic compounds were found to be effective for the treatment of schizophrenia and other psychotic disorders. These "typical" antipsychotic compounds function as antidopaminergic agents, primarily blocking the dopamine 2 (D2) receptors of the central nervous system, and are widely prescribed for the treatment of psychotic disorders. When used in the treatment of psychotic disorders, the compounds function to very effectively reduce "positive symptoms" of schizophrenia and related psychotic disorders, including delusions and hallucinations.

Typical antipsychotic compounds are well-known in the art and include drugs derived from phenothiazines, such as thioridazine and perphenazine; butyrophenone-derived compounds, such as haloperidol (Haldol); and compounds of the diphenylbutylpiperdine group, such as pimozide. The precise chemical compositions and configurations of these compounds can be found in the Merck Index, $12^{th}$ ed., 1996, and are incorporated herein by reference. The compounds are dopamine antagonists, binding to dopamine (D2) receptors, thereby blocking the receptors and reducing or preventing receptor-dopamine binding.

The side effects caused by the typical antipsychotics are considerable, and can be life-threatening. Patients may suffer from akathisia, dystonias, muscle rigidity and shuffling gait, some of which is irreversible. Significant weight gain is a side effect also associated with the use of typical antipsychotics. The frequent occurrence of uncomfortable or unmanageable side effects often results in reduced compliance with, or increased cost of, the drug treatment regime.

Recently new compounds for use in the treatment of psychotic disorders have been developed. These compounds, designated "atypical" antipsychotics, to distinguish them from the "typical" or older antipsychotic medications, are primarily benzisoxals, and are characterized by their antagonistic action on multiple receptors, including the serotonin (5HT2) receptors and the dopamine (D2) receptors of the central nervous system. Some of the compounds, including risperidone, also act as blockers of the central andrengeric receptors. The current list of atypical antipsychotic drugs is well known in the art and includes, but is not limited to, clozapine (Clozaril®), olanzapine (Zyprexa®) quetiapine (Seroquel®) and ziprasidone. The precise chemical compositions and configurations of these compounds can be found in the Merck Index, 12$^{th}$ ed., 1996, and are incorporated herein by reference.

An additional atypical antipsychotic, also well known in the art, is risperidone, sold under the trade name "Risperdal®" by Janssen Pharmaceuticals of Beerse, Belgium. Classified as a benzisoxazol and an atypical antipsychotic, risperidone has the properties to not only block D2 receptors, but 5HT2 receptors as well. This medication is extensively metabolized in the liver by the cytochrome P450IID6 to the principle metabolite, 9-hydroxyrisperidone. Further chemical properties and the structure of risperidone are discussed in U.S. Pat. No. 4,804,663 to Kennis et al., issued Feb. 14, 1989, entitled "3-piperidinyl-substituted 1,2,-benzisoxazoles and 1,2-benzisothiazoles," the contents of which are incorporated herein by reference. The chemical designation of risperidone is 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one. Its molecular formula is $C_{23}H_{27}FN_4O_2$ and its molecular weight is 410.49. The structural formula of risperidone is:

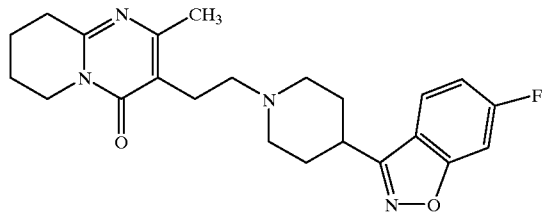

Like their "typical" counterparts, the atypical antipsychotics have been shown to reduce the occurrence of "positive" side effects in individuals suffering from psychotic disorders. They also have been shown to reduce the "negative" symptoms of schizophrenia, including social isolation, emotional withdrawal, decreased motivation, and subnormal communication and social skills.

With some exceptions, the side effect profiles of the atypical antipsychotics are highly favorable compared to those of the typical antipsychotics. However, clozapine reduces white blood cell counts, so its administration must be accompanied by costly blood tests to monitor for potentially fatal agranulocytosis. Olanzapine has been shown to cause significant weight gain, in some cases up to 1 pound per week and is, therefore, not particularly suitable for use in a population of patients specifically fearing weight gain. Quetiapine has been shown to cause cataract formation in some mammals. In contrast, risperidone has been shown to have few of these side effects. White blood cell count remains unaffected and weight gain is minimal. The few side effects attributable to risperidone can be easily monitored and corrected.

It would be highly desirable to develop an effective method of treating Bulimia Nervosa and Bulimia-Type Eating Disorder N.O.S. utilizing a pharmacological agent that is not cost prohibitive, and the administration of which does not result in significant side effects, including weight gain. The present invention achieves this objective through the use of known, relatively safe atypical antipsychotic medications as a treatment modality for eating disorders such as Bulimia Nervosa and Bulimia-Type Eating Disorder N.O.S. More specifically, the present invention achieves this objective through use of the specific atypical antipsychotic risperidone, which possesses pharmacological properties and a side effect profile particularly suitable for use in the treatment of Bulimia Nervosa and Bulimia-Type Eating Disorder N.O.S.

SUMMARY OF THE INVENTION

The present invention relates to the treatment of eating disorders through the use of atypical antipsychotic medications. One aspect of the invention is a method of treating Bulimia Nervosa and Bulimia-Type Eating Disorder N.O.S. in a human patient by administration of a pharmaceutically effective amount of any one of the atypical antipsychotic medications known in the art. In a second aspect, the invention is directed to a method of treating Bulimia Nervosa and Bulimia-Type Eating Disorder N.O.S. in a human patient by administration of a pharmaceutically effective amount of the atypical antipsychotic medication risperidone. The invention is further directed to a method of treatment of Bulimia Nervosa and Bulimia-Type Eating Disorder N.O.S. by administration of a dosage of about 0.1 to about 4.0 milligrams per day of the atypical antipsychotic medication risperidone, or of a dosage of about 1.0 to about 2.0 milligrams of risperidone per day. Alternatively, this invention is directed to a method of treatment of Bulimia Nervosa and Bulimia-Type Eating Disorder N.O.S. by administration of a dosage of about 0.1 to about 1.1 milligrams per day of the atypical antipsychotic medication risperidone or of a dosage of about 0.5 to about 1.1 milligrams of risperidone per day. The dosage can be administered in any form suitable to the patient, including, but not limited to, oral, intramuscular (M), rectal (PR) and transdermal dosage forms, or other forms known in the art. The dosage form may also be selected from the group consisting of sustained release forms, controlled release forms, delayed release forms and response release forms.

DETAILED DESCRIPTION OF THE INVENTION

The present invention relates to the treatment of individuals diagnosed with Bulimia Nervosa and Bulimia-Type Eating Disorder N.O.S. by the administration of any one of the atypical antipsychotic medications.

To practice this development, a patient diagnosed with either Bulimia Nervosa or Bulimia-Type Eating Disorder N.O.S. is given a pharmaceutically effective dose of any one or more atypical antipsychotic medications. Any atypical antipsychotic medication, or any combinations of any such antipsychotic medications, may be utilized. Thus, this method contemplates, but is not limited to, the use of the currently-known atypical antipsychotic medications: clozapine, risperidone, olanzapine, quetiapine and ziprasidone. Other atypical antipsychotic medications should confer the same benefit, provided they operate upon the same physiological systems described herein.

The particular antipsychotic medication or medications utilized is determined by the physician on a case by case basis, through a process well known in the art which incorporates evaluation of such factors as the patient's medical history, personality, body mass and tolerance for specific side effects. Determination of a "pharmaceutically effective dosage" is also made by the treating physician who, using a method well known in the art, determines the amount which effectively treats the individual's symptoms of the eating disorder, and which either results in an absence of negative side effects or in an occurrence of such side effects at a minimal level such that the benefits experienced by the patient are not outweighed. In general, the term "pharmaceutically acceptable" as used herein, is meant that the drug-active compounds and other ingredients used in the present methods are suitable for use in contact with the tissue of humans without undue toxicity, irritation, allergic response and the like, commensurate with a reasonable benefit/risk ratio.

Dosages may be administered orally, in liquid or pill form, or via any other suitable means known in the art including, but not limited to, intramuscular injection. The duration of treatment will vary from patient to patient and will be determined by the treating physician. Treatment with antipsychotic medications as described above may be combined with any other type of pharmacological or behavioral therapy known in the art for the treatment of Bulimia Nervosa or Bulimia-Type Eating Disorders N.O.S., including but not limited to antidepressant medications, anticonvulsant medications, mood stabilizer, such as lithium, cognitive behavioral therapy, individual and group psychotherapy, and relaxation techniques.

In a particular embodiment of the invention, the atypical antipsychotic risperidone is administered to the patient in a pharmaceutically effective amount. Typical dosages are from about 0.1 milligram per day to about 4 milligrams per day. In another embodiment of the invention, risperidone is administered to the patient in extremely low does, in order to minimize side effects. Such dosage may consist of from about 0.1 milligram to about 1.1 milligrams of risperidone per day, or from about 0.5 to about 1.1 milligrams per day. Alternatively, the dosage given the patient may consist from about 0.1 milligram to about 2.0 milligrams of risperidone per day.

Administration of the atypical antipsychotic to the patient may be accomplished by any means known in the art. The dosage can be administered in any form suitable to the patient, including, but not limited to, oral, intramuscular (IM), rectal (PR) and transdermal dosage forms, or any other forms known in the art. The dosage form may also be selected from the group consisting of sustained release forms, controlled release forms, delayed release forms and response release forms.

The following non-limiting example will serve to further illustrate the above-described method.

EXAMPLE 1

An 18-year old single Caucasian female ("SM") presents to a psychiatrist upon referral of her primary care doctor. The psychiatrist is asked to assess the patient and make recommendations for treatment.

SM reports an 8-month history of consuming enormous amounts of food (approximately 5,000 calories, primarily in carbohydrate form) in a discrete amount of time (less than one hour) approximately two times per day. When questioned, she confides that she feels a lack of control over what she is consuming. As a result, she states, "I am scared to death of gaining weight [following these binges]." Therefore, she self-induces vomiting in order to avoid weight gain.

SM describes herself as "obese", and "revolting to look at", although no body characteristic in particular causes her distress. She feels like a "failure at everything" because of her perceived size. When asked to draw a picture of her body form on paper, she clearly exaggerates her body size.

Past Psychiatric history indicates that she was diagnosed by her Primary Care Doctor with Major Depression approximately 4 months ago. At that time, she was started on fluoxetine 20 mg PO qam and has been compliant with the regimen. (She is not interested in psychotherapy or behavioral therapy). SM relates that she has had remission of depressive symptoms by both Zung Depression Scores (shows depression in the mild range) and self-reported alleviation of anhedonia, insomnia, memory and concentration problems and low energy level. Her bingeing and purging has not subsided despite a therapeutic trial of an antidepressant. She has been keeping a journal of her bulimic activities on the advice of her physician for the past month.

Due to her continued symptoms, SM agrees to participate in an open trial of risperidone for the treatment of Bulimia Nervosa. Informed consent is obtained from the patient. After a complete physical examination, baseline laboratory studies and rating scale scores are completed, she begins treatment. She is asked to continue keeping a journal of her bulimic behaviors during the trial. She will be seen bi-weekly by the Psychiatrist and monitored for efficacy and side effects of the medication.

Treatment is initiated at 0.5 mg PO twice per day of risperidone. She continues fluoxetine at her current dosage of 20 mg PO QAM. She is seen after two weeks of therapy and reassessed. Vital signs and weight are measured, and laboratory studies are conducted per protocol. She has not had any cessation of symptoms by that time. Risperidone dosage is then changed to 1.5 mg PO to be given at bedtime.

At week four she is reassessed. At this time, laboratory studies are conducted per protocol. Vital signs and weight are measured. Upon review of the patient's journal, the Psychiatrist notes that there is a 30% reduction in bulimic symptomatology. She reports no side effects to the medications at this time. She is maintained at 1.5 mg PO QHS, and is seen at 6 and 8 weeks from initiation of therapy thereafter. Vitals, weight, and laboratory studies are repeated per protocol.

At the conclusion of the 8-week study, she completes self-rating scales for depression, anxiety and body image. There are no appreciable differences in baseline and final scores of the anxiety and depression scales. However, body image scores have improved by 50%. Her journal entries indicate that she has had a 50% improvement in bulimic symptomatology.

She is referred back to her primary care doctor for continued treatment of her disorder with risperidone and fluoxetine.

We claim:

1. A method of treating human beings suffering from Bulimia Nervosa or Bulimia-Type Eating Disorder Not Otherwise Specified comprising the administration thereto of a pharmaceutically effective amount of one or more atypical antipsychotic medications selected from the group consisting of risperidone, clozapine, olanzapine, quetiapine and ziprasidone.

2. A method according to claim 1 wherein said pharmaceutically effective amount comprises from about 0.1 to about 4.0 milligrams of the medication per day.

3. A method according to claim 1 wherein said pharmaceutically effective amount comprises from about 0.1 to about 2.0 milligrams of the medication per day.

4. A method according to claim 1 wherein said pharmaceutically effective amount comprises from about 0.1 to about 1.1 milligrams of the medication per day.

5. A method according to claim 1 wherein said pharmaceutically effective amount comprises from about 0.5 to about 1.1 milligrams of the compound per day.

6. A method of according to claim 1 wherein a pharmaceutically effective amount is administered to said human being in a form selected from the group consisting of sustained release forms, controlled release forms, delayed release forms, and response release forms.

7. A method according to claim 1 wherein a pharmaceutically effective amount is administered to said human being in oral dosage form.

8. A method according to claim 1 wherein a pharmaceutically effective amount is administered to said human being in intramuscular dosage form.

9. A method according to claim 1 wherein a pharmaceutically effective amount is administered to said human being in rectal dosage form.

10. A method according to claim 1 wherein a pharmaceutically effective amount is administered to said human being in transdermal dosage form.

11. A method of treating human beings suffering from Bulimia Nervosa and Bulimia-Type Eating Disorder Not Otherwise Specified comprising the administration thereto of a pharmaceutically effective amount of a compound having the chemical structure:

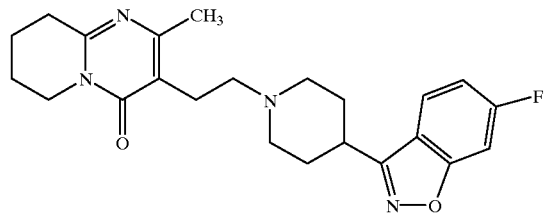

12. A method according to claim 11 wherein said pharmaceutically effective amount comprises from about 0.1 to about 4.0 milligrams of the compound per day.

13. A method according to claim 11 wherein said pharmaceutically effective amount comprises from about 0.1 to about 2.0 milligrams of the compound per day.

14. A method according to claim 11 wherein said pharmaceutically effective amount comprises from about 0.1 to about 1.1 milligrams of the compound per day.

15. A method according to claim 11 wherein said pharmaceutically effective amount comprises from about 0.5 to about 1.1 milligrams of the compound per day.

16. A method according to claim 11 wherein a pharmaceutically effective amount is administered to said human being in oral dosage form.

17. A method according to claim 11 wherein a pharmaceutically effective amount is administered to said human being in intramuscular dosage form.

18. A method according to claim 11 wherein a pharmaceutically effective amount is administered to said human being in rectal dosage form.

19. A method according to claim 11 wherein a pharmaceutically effective amount is administered to said human being in transdermal dosage form.

20. A method of according to claim 11 wherein a pharmaceutically effective amount is administered to said human being in a form selected from the group consisting of sustained release forms, controlled release forms, delayed release forms, and response release forms.

* * * * *